United States Patent [19]

Casper et al.

[11] Patent Number: 5,692,496
[45] Date of Patent: Dec. 2, 1997

[54] DRY POWDER MEDICAMENT INHALATOR HAVING AN INHALATION-ACTIVATED FLOW DIVERTING MEANS FOR TRIGGERING DELIVERY OF MEDICAMENT

[75] Inventors: Robert A. Casper, Raleigh; Frank A. Leith; David L. Gardner, both of Chapel Hill, all of N.C.

[73] Assignee: Innovative Devices, LLC, Raleigh, N.C.

[21] Appl. No.: 690,989

[22] Filed: Aug. 1, 1996

Related U.S. Application Data

[60] Provisional application No. 60/001,786, Aug. 2, 1995.

[51] Int. Cl.⁶ .................................................. A61M 16/00
[52] U.S. Cl. .............................. 128/203.15; 128/203.12; 128/203.21; 128/200.24; 604/58
[58] Field of Search .................. 128/203.12, 203.15, 128/203.21, 200.22, 200.21, 200.24; 604/58

[56] References Cited

U.S. PATENT DOCUMENTS

| | | | |
|---|---|---|---|
| 3,807,400 | 4/1974 | Cocozza | 128/266 |
| 3,906,950 | 9/1975 | Cocozza | 128/266 |
| 3,991,761 | 11/1976 | Cocozza | 128/266 |
| 4,013,075 | 3/1977 | Cocozza | 128/266 |
| 4,627,432 | 12/1986 | Newell et al. | 604/58 |
| 4,664,107 | 5/1987 | Wass | 604/58 |
| 4,667,668 | 5/1987 | Wetterlin | 128/203 |
| 4,668,218 | 5/1987 | Virtanen | 604/58 |
| 4,805,811 | 2/1989 | Wetterlin | 222/337 |
| 5,201,308 | 4/1993 | Newhouse | 128/203.15 |
| 5,320,714 | 6/1994 | Brendel | 128/203.15 |
| 5,388,572 | 2/1995 | Mulhauser et al. | 128/203.15 |
| 5,447,151 | 9/1995 | Bruna et al. | 128/203.15 |
| 5,482,032 | 1/1996 | Smith et al. | 604/58 |

FOREIGN PATENT DOCUMENTS

| | | | |
|---|---|---|---|
| 0 211 595 A2 | 2/1987 | European Pat. Off. | A61M 15/00 |
| 0 455 463 A1 | 11/1991 | European Pat. Off. | A61M 15/00 |
| 0 467 172 A1 | 1/1992 | European Pat. Off. | A61M 15/00 |
| 40 20 571 A1 | 1/1992 | Germany | A61K 9/72 |
| 41 33 274 A1 | 2/1993 | Germany | A61M 15/00 |
| 9013328 | 11/1990 | WIPO | 128/203.15 |
| WO 93/12831 | 7/1993 | WIPO | A61M 15/00 |

Primary Examiner—V. Millin
Assistant Examiner—V. Srivastava
Attorney, Agent, or Firm—Thorpe, North & Western, LLP

[57] ABSTRACT

An inhalation-activated inhalator having a flow diverting means wherein the primary air flow channel is blocked for a brief period during inspiration with air flow during that period passing through a dosing chamber arrangement and connecting passage to inject medicament into the inspired air stream is provided. By diverting the inspired air stream in this fashion, powdered medicament may be provided for inhalation at a particular point in the patient's inspiration cycle, thereby optimizing the delivery of medicament to the lungs.

10 Claims, 2 Drawing Sheets

DRY POWDER MEDICAMENT INHALATOR HAVING AN INHALATION-ACTIVATED FLOW DIVERTING MEANS FOR TRIGGERING DELIVERY OF MEDICAMENT

RELATED APPLICATIONS

This is an application filed under 35 U.S.C. §111(a) for an invention which was disclosed in Provisional application Ser. No. 60/001/786, filed under 35 U.S.C. §111(b) on Aug. 2, 1995, no more than twelve (12) months from the filing date of this §111(a) application.

TECHNICAL FIELD

The present invention relates to a medicament inhalator, and more particularly, to a dry powder medicament inhalator usable by asthmatics and the like. By inhaling on a mouthpiece, a prescribed dosage of medicament, housed in a dosing cartridge in attachment to the inhalator, becomes available to the patient during inspiration and is deposited in the lungs of the user.

BACKGROUND ART

There are essentially two classes of inhalation devices currently available in the marketplace for the administration of a powdered medicament to the lungs. The predominant inhalation device is a pressurized, metered dose inhaler containing a suspension of drug in a pharmaceutically inert liquid propellant, e.g., chlorofluorocarbons or fluorocarbons. Inhalation devices of this type are well known.

These propellant-based inhalation devices have the property of consistently delivering a predetermined dose of medication from the aerosol canister. However, the drug particles are propelled at high velocity from the inhalation device and some medication impacts in the mouth or in the throat of the patient, becoming unavailable for deposition in the lungs. Further, growing concern over the link between depletion of atmospheric ozone and the chlorofluorocarbons emitted from these inhalers has focused attention on the development of alternative means of delivering medication to the lungs, including the development of dry powder inhalation systems.

Dry powder inhalers represent the second major class of inhalation devices. Dry powder inhaler devices known to the applicants and existing in the marketplace utilize the patient's inhaled breath as a vehicle to transport the dry powder drug to the lungs. Presently there are four principal methods in use to provide fine particulate powder to the lungs without the use of propellants.

The first method available relies on the use of a hard gelatin capsule which contains a premeasured dose of therapeutically active material and an inhalator device for use with the capsule. The capsule is placed in the inhalator device which serves to open or perforate the capsule, exposing the dose of medicament. The medicament is removed from the capsule, by the vacuum action created when the patient inhales through the mouthpiece of the device, and is entrained in the inspired air stream for transport to the patient's lungs. The empty capsule is removed from the inhalation device after use. Inhalators using this type of capsule technology are described in U.S. Pat. No. 3,906,950 to Cocozza; U.S. Pat. No. 4,013,075 to Cocozza; U.S. Pat. No. 3,807,400 to Cocozza; and U.S. Pat. No. 3,991,761 to Cocozza. The intent in each of these devices is to remove all of the powdered medicament from the interior of the capsule. However, it has been found that the air stream generated by the patient is typically insufficient to accomplish complete removal of medicament from the capsule. Further, gelatin capsules are affected by relative humidity on storage and may become hydrated, resulting in poor opening of the capsule and agglomeration of the powder contents, or dehydrated, resulting in brittle fracture of the capsule, potentially making fine gelatin fragments available for inhalation or compromising dosing due to electrostatic attraction of medicament to the capsule surfaces.

A second method for delivering of dry powder medicaments relies on providing a package containing multiple doses of medicament, each contained in a sealed blister. The package is used in conjunction with a specially designed inhalation device which provides a means of attachment for the package and perforation of an individual blister by the patient prior to the inhalation of its contents. Delivery systems of this type are described in EPO Patent Application Publication No. 0 211 595 A2 to Newell et al.; EPO Patent Application Publication No. 0 455 463 A1 to Velasquez et al.; and EPO Patent Application Publication No. 0 467 172 A1 to Cocozza et al. As the patient inhales, a portion of the inhaled air stream flows continuously through the perforated blister entraining the medicament and providing for inclusion of the medicament in the inspired breath. Delivery of medicament to the patient's inspired air stream begins as sufficient flow develops through the blister for removal of the medicament. No means is provided by which the point or rate of delivery of medicament to the patient is controlled.

A third method for delivery of dry powder medicaments involves the use of a device equipped with a drug reservoir containing sufficient medicament for a much larger number of doses. The Draco TURBUHALER® is an example of this type of device and is described in detail in U.S. Pat. No. 4,668,218 to Virtanen; U.S. Pat. No. 4,667,668 to Wetterlin; and U.S. Pat. No. 4,805,811 to Wetterlin. The device provides a means for withdrawing a dose of medicament from the reservoir and preparing the withdrawn dose for inhalation by the patient. As the patient inhales through the mouthpiece of the device, the medicament contained in perforations in a dosing plate is entrained in the inspired air and flows through a conduit or conduits, which serve as a vortex creating means for breaking up powder agglomerates, before becoming available to the patient. Moisture ingress of the reservoir results in agglomeration of the powder contents, compromising dosing due to retention of powder in the perforations in the dosing plate and potentially inadequate breakup of particulates in the inspired air stream.

A fourth method for delivery of dry powder medicaments involves the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device. Devices of this general type are described in PCT WO 93/12831 to Zirerenberg et al.; German Patent No. DE 4133274 A1 to Kühnel et al.; German Patent No. DE 4020571 A1 to Hochrainer et al.; and U.S. Pat. No. 5,388,572 to Mulhauser et al. The incorporation of a piston system, in each case, adds to the complexity of the inhalation device, both in terms of use by the patient and device manufacturability.

The present invention avoids many of the problems associated with the prior art, providing a means by which the administration of powdered medicament may be controlled by the patient's inspiratory flow, optimizing powder deaggregation and deposition in the lungs, while maintaining simplicity of device design and use by the patient.

OBJECTS OF THE INVENTION

It is the object of the present invention to provide an inhalation device for the administration of dry powder medicaments which provides a means of diverting inspiratory flow from the main inhalation channel of the device for a brief period during inspiration, the inspiratory flow during that period passing instead through a dosing circuit arrangement and picking up dry powder medicament for presentation to the patient, with the subsequent inspiratory flow again passing, in part or in total, through the main flow channel of the device.

It is another object of this invention to provide a flow diverting means, to switch the air flow from the main inhalation channel to the dosing circuit and back again, operating as a consequence of the patient achieving a predetermined inspiratory flow rate, in order to optimize the deposition of the dry powder medicament in the lungs of the patient.

It is another object of this invention to provide a replaceable dosing cartridge containing powdered medicament for use with the inhalation device, the cartridge containing discrete doses of medicament distributed on and along a windable tape.

It is another object of this invention to provide a replaceable dosing cartridge containing powdered medicament for use with the inhalation device, the cartridge containing discrete doses of medicament distributed on a dosing wheel or disc.

It is another object of this invention to provide an alternative replaceable dosing cartridge containing bulk powdered medicament in a reservoir, with withdrawal of medicament from the reservoir being achieved by the patient at the time of use.

It is another object of this invention to provide powdered medicament in a single unit dose for use with the inhalation device, independent of a multiple dose cartridge.

It is yet another object of this invention to provide a means by which individual blisters on the windable tape or individual doses on a dosing wheel or disc may be penetrated through allowing the diverted inspiratory flow to pass into and then out of a blister, entraining the powdered medicament during this process.

It is another object of this invention to provide an impaction surface, within the dosing circuit, which may be contacted by the entrained dry powder medicament to maximize breakup of powder aggregates.

Some of the objects of the invention having been stated hereinabove, other objects will become evident as the description proceeds, when taken in connection with the accompanying drawings as best described hereinbelow.

SUMMARY OF THE INVENTION

The invention provides a means of mechanically diverting inspiratory flow from the intake of the main air flow passageway of a dry powder inhaler device for a brief period of time during inspiration, the flow passing instead through an intake and airflow channel associated with the dosing circuit of the device to provide a means of removing dry powder medicament from a blister (or other unit dose packet) and/or holding chamber and presenting the medicament to the patient for inhalation and deposition in the lungs. The dosing circuit further provides a holding chamber for receiving powdered medicament and an impaction surface downstream from the holding chamber to aid powder deaggregation.

DETAILED DESCRIPTION OF THE INVENTION

Figure 1:
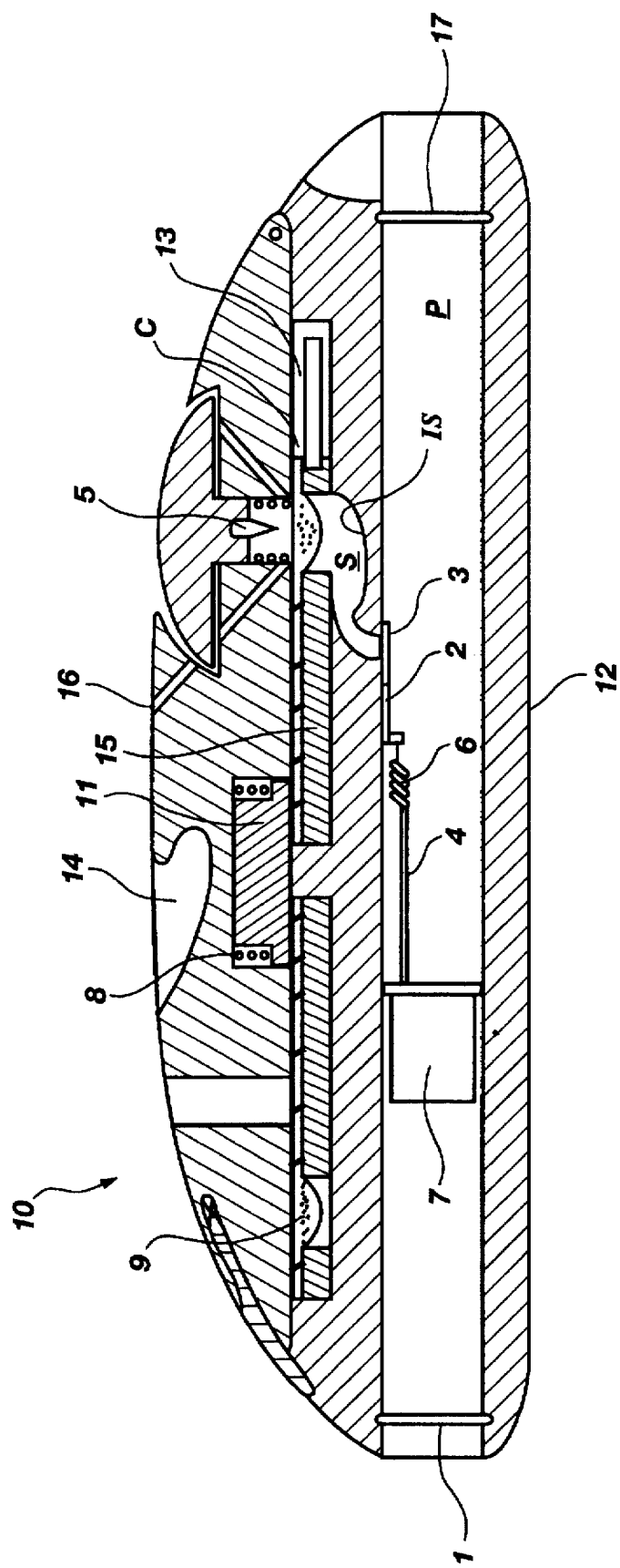
FIG. 1 of the drawings is a vertical cross sectional view of the inhalator of the invention.
Figure 2:
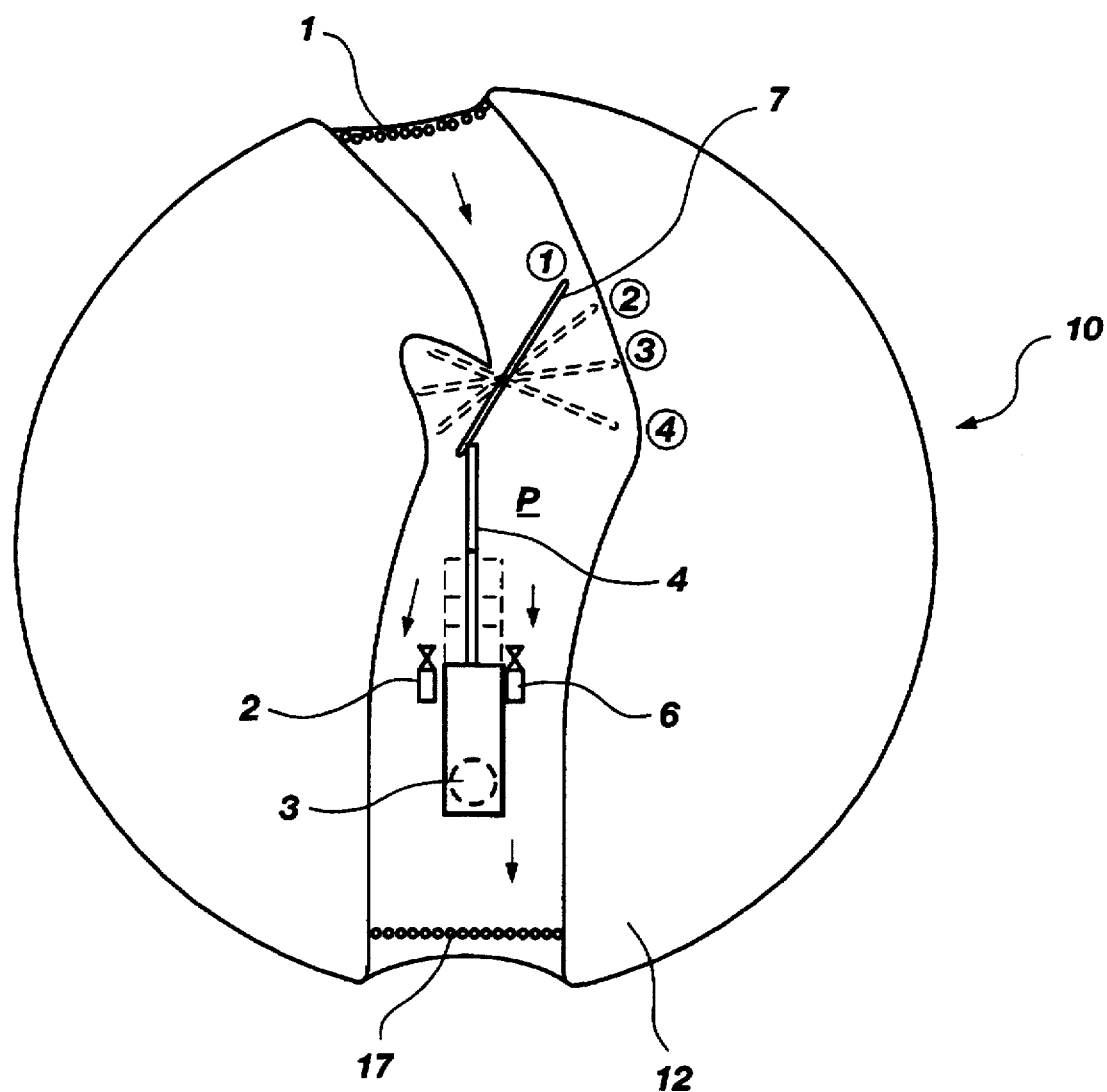
FIG. 2 of the drawings is a horizontal cross sectional view of the inhalator of the invention.

Referring now more specifically to the drawings, a preferred embodiment of a dry powder dosage inhalator according to the present invention is shown in FIGS. 1 and 2 and generally designated 10. Inhalator 10 comprises a housing 12 which is preferably formed from a plastic material although housing 12 may be made of any suitable material and is not limited to plastic. Housing 12 includes a receiving cavity C and associated mechanisms for the attachment of a replaceable, drug loaded cartridge 9 and penetrator 5 which serves to puncture through the upper and lower surfaces of the medicament containing blister or unit dose packet. Cartridge 9 is held compressed against cartridge receiver 15 under the action of compressing spring 8 and piston member 11. As known in the art and shown in FIG. 1, inhalator 10 is provided with contour 14 for the patient to place a finger in order to lift up the top of inhalator 10 and thereby open inhalator 10 so that the patient can insert cartridge 9.

The portion of housing 12 through which air flows during inhalation includes primary air circuit P and secondary air circuit S as best seen in FIGS. 1 and 2. As will be appreciated with particular reference to FIG. 1, primary air circuit P defines a restriction therein, an air flow restricting flap 7, movable under the action of air flowing from the intake of primary air circuit P, which operates through the range of this restriction. Secondary air flow circuit S comprises a holding chamber and connection passage, including impaction surface IS, and intersects and joins with primary air circuit P at a point downstream of restriction 7 defined in primary air circuit P. Disposed at the entrance end and exit end of primary air circuit P are, respectively, screen 1 and screen 17, wherein, as is known in the art of inhalators, screen 1 serves to prevent extraneous material from being sucked into primary air circuit P during inhalation on the inhalator by the patient and screen 17 serves to deaggregate the medicament during inhalation on the inhalator by the patient.

Air flow restricting flap 7 is mechanically coupled to blocking plate 3 by linkage 4. Blocking plate 3 is held in alignment by plate guide 2 which is attached to the inner surface of primary air flow circuit P. Blocking plate 3 is normally held in such a position as to maintain secondary air flow circuit S in the closed position under the action of biasing (return) spring 6.

In using the device, the patient rotates drug containing cartridge 9 to the "next-blister-ready" position by sliding indexing advance 13 thereby placing a fresh, drug containing blister in connection over secondary air flow circuit S. The blister is then penetrated by depressing penetrator element 5, thereby providing a fluid connection between the interior of the penetrated blister and secondary air flow circuit S. The patient then places the inhalator 10 to his lips and begins to inhale.

At the beginning of the inhalation, all air passes (see arrows in FIG. 2) through primary air flow circuit P, air flow through secondary air flow circuit S being prevented by the action of blocking plate 3. As air flow through the inhalator increases, the pressure of the flowing air begins to rotate air flow restricting flap 7 within the primary air flow circuit P. Rotation of air flow restricting flap 7, from position (1) to position (2) to position (3) to position (4) as indicated in FIG. 2, causes retraction of blocking plate 3, via linkage 4 and biasing spring 6, toward the distal end of primary air flow channel.

As air flow restricting plate 7 rotates through its positions and stops at the maximal restriction position (4) in primary air flow channel P, a major portion of the air flowing through primary air flow channel P is blocked from passage, and, simultaneously, blocking plate 3 approaches and stops at its point of maximum retraction and opens secondary air flow circuit S so that make-up air flows vigorously through make-up air slots 16. Air passes through the make-up air slots 16 through the penetrations in the drug containing blister and on through secondary air flow channel S, entraining drug in the process and presenting the entrained drug for inhalation through primary air flow channel P.

At this point, air flow restricting flap 7 has rotated to its fully open, stopped position (4) and air flow occurs both through primary air flow channel P and secondary air flow channel S. Drug particulate is deaggregated under the action of the vigorous entrainment air flow through secondary air flow channel S and impaction on impaction surface IS contained in secondary air flow channel S and may be further deaggregated on contacting the metallic or plastic screen 17 located in primary air flow channel P at the entrance to the inhalator mouthpiece end of inhalator 10.

After inhalation is completed, air flow restricting flap 7 counter rotates to its normal resting position (1) in primary air flow channel P under the retractive action of blocking plate return spring 6. Blocking plate return spring 6 also acts to return blocking plate 3 to its normally closed position, thereby blocking the fluid connection between secondary air flow circuit S and primary air flow circuit P.

Among the dry powder medicaments which are suitable for administration with the inhalator of the present invention are those currently administered by inhalation, such as Beta-2-stimulants, anticholinergic drugs, corticosteroids, antiallergic drugs and miscellaneous drugs used to treat respiratory disorders. For example, Beta-2-stimulants include, but are not limited to, albuterol, salmeterol, fenoterol, pirbuterol, reproterol, imiterol, terbutaline, tulobuterol, isoprenaline and oxaprenaline; corticosteroids include, but are not limited to, fluticasone propionate, beclomethasone dipropionate and budesonide; antiallergic drugs include, but are not limited to, sodium cromoglycate, ketotifen and nedocromil sodium; and miscellaneous drugs include, but are not limited to amiloride and uridine triphosphate.

It will be understood that various details of the invention may be changed without departing from the scope of the invention. Furthermore, the foregoing description is for the purpose of illustration only, and not for the purpose of limitation—the invention being defined by the claims.

What is claimed is:

1. A dry powder medicament inhalator comprising (I) a cavity for receiving a dry powder medicament packet, (II) a primary airflow circuit having an entrance and an exit for enabling air to flow therethrough, and (III) a secondary airflow circuit, the two circuits being fluidly connected to each other, and the primary airflow circuit having disposed therein an air restricting flap (i) that is movable, from a normal resting position to a maximally restricted position which blocks a major portion of airflow through the primary airflow circuit, by airflow provided in the primary airflow circuit from inhalation by a patient on the inhalator, and (ii) that is connected by a biasing spring to a movable blocking plate, such that:

(A) when the flap is in its normal resting position simultaneously the plate is in its normal resting position and blocks fluid connection between the primary airflow circuit and the secondary airflow circuit, whereby airflow through the secondary circuit is prevented, and (B) when the flap is in a restricted position from being moved by airflow provided in the primary airflow circuit from inhalation by a patient on the inhalator simultaneously the plate is moved by the flap, via the biasing spring, to a retracted open position and opens fluid connection between the primary airflow circuit and the secondary airflow circuit, whereby airflow occurs both through the primary airflow circuit and the secondary airflow circuit, and whereby the cavity as fluid connection with the primary airflow circuit via the secondary airflow circuit.

2. The inhalator of claim 1, wherein the secondary airflow circuit includes an impaction surface.

3. The inhalator of claim 1, further including a dry powder medicament containing packet disposed in the cavity in the inhalator.

4. A method for providing dry powder medicament to the lungs of a patient during inhalation, said method comprising:

(A) providing a dry powder medicament inhalator comprising (I) a cavity configured for receiving a dry powder medicament, (II) a primary airflow circuit having an entrance and an exit for enabling air flow through the inhalator, and (III) a secondary airflow circuit, the two circuits being fluidly connected to each other, and the primary airflow circuit having disposed therein an air restricting flap (i) that is movable from a normal resting position to a maximally restricted position that blocks a major portion of airflow through the primary airflow circuit, and (ii) that is connected by a biasing spring to a movable blocking plate;

(B) providing airflow in the primary circuit from inhalation by a patient on the inhalator to move the flap from (i) its normal resting position, where simultaneously the plate is also in its normal resting position and blocks fluid connection between the primary airflow circuit and the secondary airflow circuit which prevents airflow through the secondary circuit, to (ii) the flap being in a restricted position, and as the flap moves, the flap simultaneously moves the plate, via the biasing spring, to a retracted open position and opens fluid connection between the primary airflow circuit and the secondary airflow circuit, which results in fluid connection of the cavity with the primary airflow circuit via the secondary airflow circuit; and (c) whereby airflow occurs both through the primary airflow circuit and the secondary airflow circuit, and entrains the powder medicament and deposits it in the lungs of the patient.

5. The method of claim 4, wherein the secondary airflow circuit includes an impaction surface.

6. The method of claim 4, wherein step (B) comprises blocking a major portion of airflow through the primary airflow circuit by moving the flap, from airflow from inhalation by the patient, to a retracted position that is the maximally restricted fully open stopped position, and simultaneously, due to moving the flap to the maximally restricted open stopped position, moving the plate, via the biasing spring, to a retracted open position that is the maximally retracted open position, thereby entraining the powdered medicament for optimum deposition in the lungs of the patient.

7. A dry powder medicament inhalator comprising:

a body having:

a medicament cartridge receiving cavity disposed within the body;

a primary air flow circuit extending through for allowing airflow through the body;

a rotatable flow restricting means disposed in the primary air flow circuit such that air passing through the primary air flow circuit moves the rotatable flow restricting means between a normal, nonrestricting position and a restricting position wherein the rotatable flow restricting means restricts air flow through the primary air flow circuit;

a secondary air flow circuit extending at least partially through the body, the secondary air flow circuit being disposed in communication with the medicament cartridge receiving cavity; and blocking means for selectingly blocking the secondary air flow circuit, the blocking means being biased in position to block air flow through the secondary air flow circuit and disposed in communication with the rotatable flow restricting means such that movement of the rotatable flow restricting means from the normal, nonrestricting position and the restricting position moves the blocking means and permits air flow through the secondary air flow circuit.

8. The apparatus of claim 7, further comprising a spring for connecting the rotatable air flow restricting means to the blocking means.

9. The apparatus of claim 7, wherein the primary air flow circuit has an entrance and an exit, the rotatable air flow restriction means being disposed between the entrance and exit, and the secondary air flow circuit being disposed in communication with the primary air flow circuit between the rotatable air flow restriction means and the exit.

10. The apparatus of claim 7, wherein the body further comprises a cavity for receiving a medicament cartridge, the cavity being disposed in fluid communication with the second air flow circuit.

* * * * *